United States Patent [19]

Markiewitz

[11] 4,404,395
[45] Sep. 13, 1983

[54] ACRYLATE PRODUCTION

[75] Inventor: Kenneth H. Markiewitz, Wilmington, Del.

[73] Assignee: ICI Americas Inc., Wilmington, Del.

[21] Appl. No.: 390,662

[22] Filed: Jun. 21, 1982

Related U.S. Application Data

[63] Continuation of Ser. No. 136,440, Apr. 2, 1980, abandoned, which is a continuation-in-part of Ser. No. 97,932, Nov. 27, 1979, abandoned.

[51] Int. Cl.³ .............................................. C07C 67/26
[52] U.S. Cl. ..................................................... 560/209
[58] Field of Search ......................................... 560/209

[56] References Cited

U.S. PATENT DOCUMENTS

| | | | |
|---|---|---|---|
| 3,399,229 | 8/1968 | Kunze et al. | 560/209 |
| 3,632,854 | 1/1972 | Randall | 560/209 |
| 3,873,602 | 3/1975 | Katzakian et al. | 560/200 |
| 3,968,135 | 7/1976 | Steele et al. | 560/209 |
| 4,017,429 | 4/1977 | Steele et al. | 560/209 |

FOREIGN PATENT DOCUMENTS

| | | |
|---|---|---|
| 1473715 | 3/1967 | France . |
| 23019 | 2/1977 | Japan ............................ 560/209 |
| 1195485 | 6/1970 | United Kingdom . |

*Primary Examiner*—Natalie Trousof
*Assistant Examiner*—L. Hendriksen

[57] ABSTRACT

An improved process for the production of hydroxy alkyl acrylates or hydroxy alkyl methacrylates which comprises adding an alkylene oxide to a solution of acrylic or methacrylic acid, at least 0.05% by weight of acid of chromium trioxide catalyst and at least 5% by weight based on acid of hydroxyalkyl acrylate or hydroxyalkyl methacrylate.

7 Claims, No Drawings

ACRYLATE PRODUCTION

This is a continuation of application Ser. No. 136,440 filed Apr. 2, 1980, now abandoned, which is a continuation-in-part of Ser. No. 97,932 filed Nov. 27, 1979 and now abandoned.

This invention concerns the production of hydroxy alkyl acrylates and methacrylates. More particularly, this invention relates to an improved method for the production of hydroxy alkyl acrylates and methacrylates by the chromium trioxide-catalyzed reaction of an alkylene oxide with acrylic or methacrylic acid.

In Steckler U.S. Pat. No. 3,875,211 there is disclosed a method wherein a trivalent chromium salt is utilized as a catalyst in the reaction of acrylic acid and alkylene oxide. U.S. Pat. No. 3,708,524 dated Jan. 2, 1973 suggests the use of a chromium compound in combination with a trivalent iron compound as catalyst in the production of hydroxy alkyl acrylates or hydroxy alkyl methacrylates. See also U.S. Pat. No. 3,632,854. None of the methods disclosed in the prior art, however, allow for the production of hydroxy alkyl methacrylates or acrylates under conditions which avoid a potential buildup of unreacted alkylene oxide while generating storage stable products of sufficient purity and freedom from deleterious amounts of catalysts. Such products allow them to be used directly as an intermediate in chemical processes such as for example, in polymerization processes for the manufacture of industrial resins.

It has now been discovered that the foregoing and related problems can be overcome by an improved process wherein the acrylic or methacrylic acid is initially mixed with an organic solvent in which the chromium trioxide catalyst is soluble followed by the sequential addition of alkylene oxide. The use of an oxide of chromium rather than any of the prior art chromium compounds, such as salts avoids the presence of foreign substances which may detrimentally affect the purity of the final product.

According to the invention there is therefore provided in a method for the preparation of a hydroxy compound selected from the group consisting of hydroxy alkyl acrylates and methacrylates by the reaction of an alkylene oxide with an acrylic component selected from the group consisting of acrylic and methacrylic acid in the presence of chromium compound, the improvement which comprises the steps of initially mixing said acrylic or methacrylic acid with at least about 0.05% by weight of the acid, of chromium trioxide and from about 5 to 20% by weight of the acid of a solvent in which the chromium trioxide is soluble, and then continually adding the alkylene oxide in a total amount of from about 0.90 to 1.5 moles of alkylene oxide to 1 mole of acrylic or methacrylic acid to the reaction mixture. The reaction may be continued till substantially all the acid is used.

The starting materials for the present invention are acrylic acid or methacrylic acid. An alkylene epoxide such as ethylene oxide, propylene oxide or butylene oxide is used as a coreactant. Normally the coreactants are used in about equal molar proportion. A preferred range suggested for the practice of the present invention is from about 0.90 to 1.5 mols of alkylene oxide to 1 mol of the acrylic or methacrylic acid. A more preferred range is about 1.00 to 1.2 mols of alkylene oxide to 1 mol of acid since a substantial excess of alkylene oxide tends to increase the formation of undesired by-products.

The reaction is preferably conducted at a temperature within the range of about 60° to 120° C. and more preferably at a temperature about 80° to 100° C. Lower temperatures provide for lower reaction rates, higher reaction temperatures tend to promote undesirable polymer formation. The reaction is normally run until the acid number of the reaction mixture has been brought below 30. An acid number of about 5 to 15 indicates that the reaction has been essentially completed. Depending on the reaction temperature and the concentration of catalyst this will occur in from about 20 to 1000 minutes, for example, 1 to 4½ hours. The longer times being necessary at lower temperatures and lower catalyst concentrations.

The catalyst to be employed in accordance with the present invention is chromium (VI) trioxide. The amount of catalyst utilized should be at least 0.05% by weight of acrylic or methacrylic acid. Naturally for economic reasons, the practitioner of the process should not utilize more catalyst than is necessary. Although it is possible to use as much catalyst as 5% by weight of acid, it should be recognized that as the amount of catalyst used is increased the resulting purity of hydroxy alkyl acrylate or methacrylate decreases. In those instances where the purity of the resulting product is not an issue, larger amounts of catalyst up to 5% may be desirable to achieve shorter reaction times. Final products having sufficient purity to allow their use without further purification for end uses such as the formation of unsaturated thermoset resins are obtained at catalyst levels of about 0.2% by weight of acid. For example, the catalyst may be present in amounts of 0.05 to 0.2% or from 0.05 to 2% based on the weight of the acid.

By premixing the acrylic or methacrylic acid, and the catalyst in an amount of solvent about 5 to 20% by weight of acid prior to the addition of alkylene oxide, the process of the invention allows the catalyst to be most effective by providing an immediate reaction which begins upon the first addition of the alkylene oxide. It has been found that when weight of starting solvent is about 15% of the amount of acid, the amount of alkylene oxide present during the reaction will not exceed a safe level of about 7 to 10% by weight of total reaction mixture if the addition rate of alkylene oxide is about 0.5% by weight of total alkylene oxide per minute. At initial solvent levels of less than 5% the reaction proceed undesirably slowly, levels above 20% provide no advantages and reduce the economic advantage of the process. This suggested initial solvent level prevents the buildup of unreacted alkylene oxide which greatly minimizes exothermic conditions and risks of explosion.

Surprisingly it has also been discovered that the catalyst can be utilized in far smaller quantities than was heretofore known for reactions of alkylene oxide and acrylic or methacrylic acid. The ability of the process to function at such low catalyst levels provides for a surprisingly pure final product.

A small amount of a polymerization inhibitor is desirably incorporated into the reaction mixture to guard against acid and acrylate or methacrylate polymerization during the course of the reaction of the alkylene oxide with acrylic or methacrylic acid, particularly when the reaction is effected at slightly elevated temperatures such as above 130° C., which would otherwise result in contamination of the reaction product with acrylate or methacrylate polymer. A number of suitable polymerization inhibitors include: hydroquinone, monomethyl ether of hydroquinone, parabenzoquinone, t-butyl catechol and others. Two particular preferred inhibitor systems utilize a combination of t-butyl catechol and monomethyl ether of hydroquinone or parabenzoquinone and monomethylether of hydroquinones. The use of dilute oxygen in the nitrogen mixtures during the reaction, improves the effectiveness of the inhibitors allowing for extended reactor cycles.

The solvents that may be employed in the reaction may be any in which the chromium (VI) trioxide is soluble and which are miscible with alkylene oxide and acrylic methacrylic acid. Suitable solvents include tetrahydrofuran, dimethyl sulfoxide, higher boiling ketones such as, methyl isobutyl ketone and diethyl ketone, dimethyl formamide, hydroxy propyl methacrylate, hydroxy propyl acrylate among others. To avoid the need for further separation techniques it is an advantage to use the final product as the solvent for chromium trioxide. A preferred solvent in a method to prepare hydroxy propylmethacrylate would be hydroxy propyl methacrylate.

Should the final product be utilized in subsequent solvent polymerization reactions additional solvents such as styrene may provide economic advantages. The products of the present invention dissolved in styrene are suitable in the manufacture of unsaturated thermosetting urethane resins such as for example those disclosed in U.S. Pat. Nos. 3,876,726 and 4,218,537.

Although the process of the present invention provides a product of sufficient purity to be immediately useful in further polymerization reactions, an even higher purity may be obtained by removing the chromium trioxide by for example a citric acid wash, a distillation or other well known purification techniques.

Since the presence of water in the hydroxy compound is considered undesirable as it affects the utility of the hydroxy compound in subsequent polymerization reactions, precautions should be employed, such as vacuum stripping, to remove substantially all the water from the coreactants of the process.

The products of the process of the invention have been found to have excellent storage stability which is defined as the length of time the products prepared in accordance with the invention may be stored at 55° C. before gellation occurs.

The present invention may be more fully understood in the following example which are offered by way of illustration. Parts by weight are used throughout unless otherwise indicated.

EXAMPLE

Preparation of Hydroxypropyl Methacrylate

A vessel was charged 4.5 pounds of hydroxy propyl methacrylate having a molecular weight of 144.17, 30 pounds (158.1 gram mols) of methacrylic acid having a molecular weight of 86.09, 9.3 gms. or 683 parts per million each of pure t-butyl catechol and hydroquinone monomethyl ether based on weight of MA charged and 17.7 gm. or 1300 ppm of chromium trioxide based on MA. The mixture was heated to 90° C. in a pressurized reactor and flushed with nitrogen followed by an evacuation. Final vacuum was released to provide an atmosphere of 5% oxygen in nitrogen to maintain the effectiveness of the inhibitor system. The methacrylic acid solution was added to the vessel where the solution was maintained at 90° C. and 40 psig. A total of 21.2 pounds (165.6 gram mols) of propylene oxide was charged at the rate of 0.5% by weight of the total charge per minute for a total addition time of 200 minutes. The reaction continued till the acid number was approximately 15, after which the reaction mixture was cooled to 40° C. Although the reaction vessel of choice was for reasons of safety a vessel that could be pressured the reaction could be conducted at atmospheric pressures.

Excess propylene oxide may be removed by an aspirator vacuum. However, small amount of residual propylene oxide in the hydroxypropylmethacrylate have been found to be beneficial to the stability of saturated thermoset resins derived from it. The final product had a conversion yield of 98% based on mmethacrylic acid and was approximately 96% pure and could be used without further purification.

What is claimed is:

1. In a method for the preparation of a hydroxy compound selected from the group consisting of hydroxy alkyl acrylates and hydroxy alkyl methacrylates by the reaction of an alkylene oxide with an acrylic component selected from the group consisting of acrylic acid and methacrylic acid in the presence of a chromium compound and previously obtained hydroxy compound, the improvement which comprises the steps of initially mixing to form a solution in the substantial absence of water said acrylic or methacrylic acid with from about 0.05% to 5% based on the weight of the acid of chromium trioxide and from about 5 to 20% by weight of the acid of previously obtained hydroxy compound and subsequent thereto continually adding the alkylene oxide to the solution in a total amount of from about 0.90 to 1.5 mols of alkylene oxide per mol of acrylic or methacrylic acid.

2. A method as claimed in claim 1 wherein the catalyst is present in an amount of 0.05 to 2% based on the weight of acid.

3. A method as claimed in claim 1 wherein the catalyst is present in an amount of 0.05 to 0.2% based on the weight of acid.

4. A method as claimed in claim 1 wherein the hydroxy compound is hydroxy propyl methacrylate.

5. A method as claimed in claim 1 wherein a temperature range of about 60° to 120° C. is maintained during the reaction for a reaction time within the range of about 1 to 4½ hours.

6. A method as claimed in claim 1 wherein the acid is methacrylic acid.

7. A method as claimed in claim 1 wherein the acrylic component is methacrylic acid and the alkylene oxide is propylene oxide and the catalyst is present in a range of about 0.10 to 1.4% based on the weight of the methacrylic acid.

* * * * *